United States Patent [19]

Baba et al.

[11] Patent Number: 5,735,799
[45] Date of Patent: Apr. 7, 1998

[54] PULSE-WAVE PROCESSING DEVICE

[75] Inventors: Norimitsu Baba; Kazuhiko Amano, both of Suwa, Japan

[73] Assignee: Seiko Epson Corporation, Tokyo, Japan

[21] Appl. No.: 295,748

[22] PCT Filed: Dec. 27, 1993

[86] PCT No.: PCT/JP93/01895

§ 371 Date: Dec. 6, 1994

§ 102(e) Date: Dec. 6, 1994

[87] PCT Pub. No.: WO94/15525

PCT Pub. Date: Jul. 21, 1994

[30] Foreign Application Priority Data

Jan. 6, 1993 [JP] Japan ........................... 666/93
Nov. 5, 1993 [JP] Japan ........................ 277001/93

[51] Int. Cl.⁶ ............................................ A61B 5/02
[52] U.S. Cl. ................................... 600/500; 600/485
[58] Field of Search ............................ 128/672, 677, 128/687, 690; 600/485, 490, 500–503

[56] References Cited

U.S. PATENT DOCUMENTS

| | | | |
|---|---|---|---|
| 4,566,463 | 1/1986 | Taniguchi et al. | 128/682 |
| 4,944,304 | 7/1990 | Nishina | 128/667 |
| 4,995,399 | 2/1991 | Hayashi et al. | 128/689 |
| 5,119,822 | 6/1992 | Niwa | 128/672 |
| 5,156,158 | 10/1992 | Shirasaki | 128/687 |
| 5,238,000 | 8/1993 | Niwa | 128/689 |

FOREIGN PATENT DOCUMENTS

| | | |
|---|---|---|
| 45841 | 3/1982 | Japan . |
| 18155 | 1/1985 | Japan . |
| 62-60534 | 3/1987 | Japan . |
| 232929 | 9/1989 | Japan . |

*Primary Examiner*—Jennifer Bahr
*Assistant Examiner*—Bryan K. Yarnell
*Attorney, Agent, or Firm*—Mark P. Watson

[57] ABSTRACT

A device includes a pulse wave detection device that detects pulse waves; a pressure detection device that detects a pressure; a pulse wave processing device; and a display of displaying pulse wave processing data and pressures. It is provided with a pulse wave detectability test device that determines the pulse wave detectability from a pressure; a pulse wave detection state notification device that notifies the operator of the pulse wave detectability status; a pulse wave/pressure storage device that temporarily stores pulse wave and pressure data; and a pulse wave/pressure comparison device that compares pulse wave and pressure data by comparing temporarily stored past data and the current data. These devices enable the operator to easily determine the pressure to be applied when measuring pulse waves, and provide improvements in the efficiency of pulse wave measurement. Further, because it can store optimal pressure values and the pulse wave data at the time of storage, and can compare present data with past data, the device allows the operator to obtain health data.

9 Claims, 8 Drawing Sheets

PULSE-WAVE PROCESSING DEVICE

BACKGROUND OF THE INVENTION

1. Field of Technology

This invention relates to a pulse wave processing device that may be used in electronic wristwatch and other small electronic devices.

2. Background Technology

Pulse waves can be detected by any of the following methods: the method of detecting changes in pressure caused in the artery by the pulsation of the heart; the method of detecting the cardiac sound produced by the pulsation of the heart; and the method of detecting changes in blood flow. In small electronic devices such as an electronic wristwatch, the method of detecting change in blood flow through the use of an optical means is especially effective. For example, an LED and other types of light-emitting devices and a phototransistor and other types of light-receiving devices can be provided, wherein the light from the photo-emitting device is directed to a finger, and either the light reflected from the finger or the light passing through the finger is input into the light-receiving device in order to detect the change in blood flow as the change in the mount of received light. This gives changes in blood flow as pulse wave signals. Pulse wave signals can be detected and processed through the use of a filter circuit, an stoplifter, or a waveform control circuit, in order to display the condition of a human body in terms of pulses or changes in pulse waves.

Even when a part of the human body is correctly set in a pulse wave sensor, the pressure exerted between the pulse wave sensor and the human body reduces the amplitude of pulse waves, and this can give a poor detection condition. Thus, a poor detection condition makes an accurate measurement impossible, and this makes it impossible to determine with confidence as to how the detected pulse waves can be treated. Several methods of displaying the detection level of pulse waves using a display device have been devised in the past (see Patent Application Publication S62-60534).

In the above type of pulse wave processing device, the output level of a pulse wave sensor is displayed using a digital level meter in order to display the detection status of pulse waves. This allows one to place the finger at an optimal position and adjust the pressure. However, because the device displays the pulse wave level, the display on the level meter changes with the pulsation of the heart. Therefore, if the pulse count is 60 per minute, discontinuities can be determined only at a rate of one per second. Therefore, the method suffers from the drawback of not being able to confirm the optimal detection condition for the detection of pulse waves.

As another consideration, the capability for obtaining other physical data (past changes in pulses, optimal pressure, and pulse wave level) will greatly aid health management. However, conventional devices do not provide a means of obtaining this type of physical data.

This invention was accomplished in light of the above consideration. It has a purpose of providing a pulse wave processing device that is capable of providing confirmation on optimal pulse wave detection conditions at all times.

SUMMARY OF THE INVENTION

The pulse wave processing device of this invention is characterized in that it is provided with a pulse wave detection means, which, when attached to a part of a human body, detects pulse waves; a pressure detection means, which detects the force exerted between the pulse wave detection means and the body; a pulse wave processing means, which processes pulse wave signals based on the output from the pulse wave detection means; a display means, which displays the results from the pulse wave detection means; and a pressure notification means, which produces a notification based on the signals detected by the pressure detection means. These means permit continuous measurement of the pulse wave detection condition. This allows the operator to easily determine the optimal pressure to apply when detecting pulse waves, and ensures an efficient, stable measurement of pulse waves.

The pulse wave processing device may detect pulse waves and the pressure by using the pulse wave detection means. Thus, the device is characterized in that the detection sensor for the pulse wave detection means and the detection sensor for the pressure detection means may be the same. This reduces the required number of sensors, and thus minimizes the hardware requirements.

The pulse wave processing device may be provided with a pulse wave/pressure separation means, which separates the output from the pulse wave detection means, which detects pulse waves and the pressure, into pulse wave signals and pressure signals.

The pulse wave processing device may be provided with a pulse wave detectability test means that tests the pulse wave detectability condition, based on the output from the pressure detection means. This makes it possible to determine whether the pulse wave signal amplification is optimal, insufficient, or excessive.

The pulse wave processing devices may be provided with a pulse wave detection condition notification means, which provides notifications on the pulse wave detection condition to the operator, based on the pulse wave detectability test means. This makes it possible to perform continuous measurement using an optimal pulse wave signal amplitude.

The pulse wave processing device may be provided with a pulse wave/pressure memory-storage means, which simultaneously and temporarily stores the pulse wave data that are output from the pulse wave processing means and the pressure that is detected by the pressing-force detection means. This allows the storage of an optimal pressure and the pulse waveform that is generated by the application of this force. This, in turn, allows one to reference past optimal pressures and pulse waveforms.

The pulse wave processing device may be provided with a pulse wave/pressure comparison means that compares past and present data that are temporarily stored pulse wave data and pressure data, obtained by the above-mentioned pulse wave/pressure storage means. This makes it possible to confirm how the optimal pressure and pulse waveforms have changed.

In the pulse wave processing device, the pressure notification means may provide notifications on pressure in analog display or digital display.

Alternatively, the pressure notification means may provide notifications on pressure in terms of color change or sound change.

Moreover, the pressure notification means may provide notifications on pressure, using voice.

In the pulse wave processing device, the pulse wave detection means detects the amount of either the reflected or transmitted light that is obtained when light is directed onto the tissue of the human body.

Other objects and attainments together with a fuller understanding of the invention will become apparent and appreciated by referring to the following description and claims taken in conjunction with the accompanying drawings.

BRIEF DESCRIPTION OF THE DRAWINGS

FIGS. 1 through 12 all relate to embodiments of the present invention.

DESCRIPTION OF THE PREFERRED EMBODIMENTS

The following is a detailed description of the present invention, with reference to drawings.

A: Configuration of the Embodiment

Figure 1:
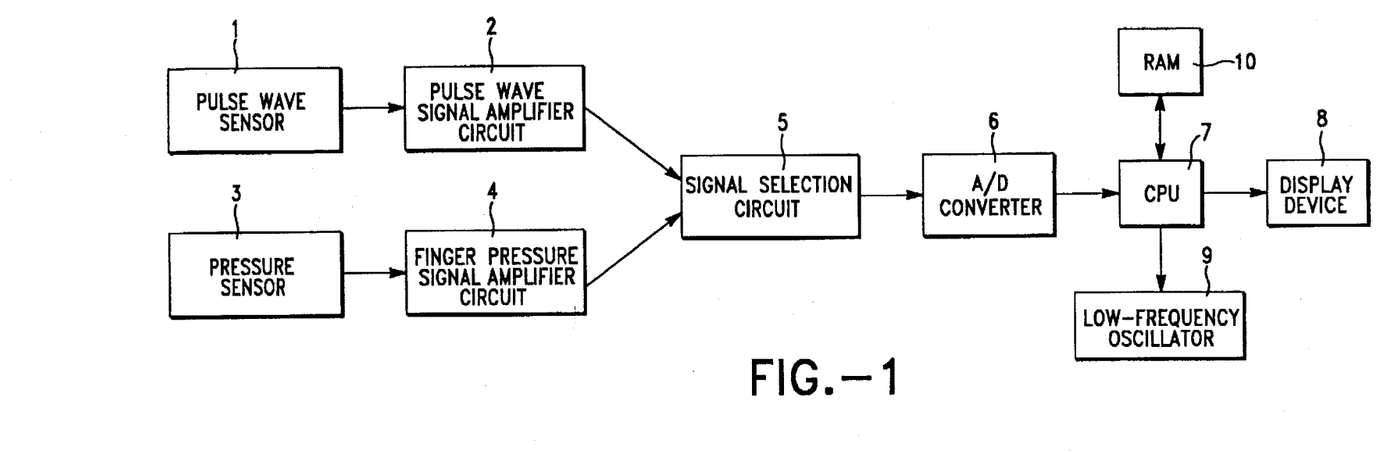
FIG. 1 is a block diagram showing the configuration of the pulse wave processing device based on an embodiment of this invention.

FIG. 1 is a block diagram showing the use of the pulse wave processing device of the present invention in a small electronic device. In the figure, 1 denotes a pulse wave sensor, such as a pressure detection sensor, a photosensor, or an ultrasonic sensor. 2 denotes a pulse wave signal amplifier circuit that amplifies the output from the pulse wave sensor 1 and which is composed of filters that remove any signals that are not a pulse wave. 3 denotes a pressure sensor, such as a strain gauge or a diaphragm. 4 denotes a pressure amplifier circuit that amplifies the output from the pressure sensor 3. 5 denotes a signal selection circuit that selects the pulse wave signals processed by the pulse wave amplifier circuit 2 and the pressure signals processed by the pressure signal amplifier circuit 4. 6 denotes on A/D converter that converts the signals selected by the signal selection circuit 5 into digital signals. 7 denotes a CPU, which, based upon the digital signals from the A/D converter, performs pulse computation processing for calculating the number of pulses per minute; pulse count comparison processing, which compares the current pulse count with specified upper and lower limits on pulse count; pulse wave analysis processing, which determines the health status from the shape of the pulse wave; and pressure test processing, which determines whether or not the pressure is at an appropriate level. The CPU also performs signal generation processing, which generates signals that are synchronized with pulses; warning signals that are generated when a pulse count falls outside a specified range; or signals indicating an abnormal health status. For the display of pulse counts and the state of the pressure, for digital display as an example, the contents to be displayed are converted to binary signals by the conversion processing and transmitted to the display device 8. 8 is a display device. For digital display, this device contains a display unit incorporating liquid crystals; it also contains a display unit drive circuit and a conversion circuit that converts the binary signals from the CPU 7 into display signals. 9 denotes a low-frequency oscillator that is provided in order to change the intervals in which sound is turned on and off according to the signals from the CPU 7, or to change the oscillation frequency. 10 denotes RAM (random access memory) that simultaneously and temporarily stores both the pulse wave data and the pressure data analyzed by the CPU 7. Using the temporarily stored data as past data, the CPU 7 reads from RAM 10, and compares them to the currently measured data.

Figure 2:
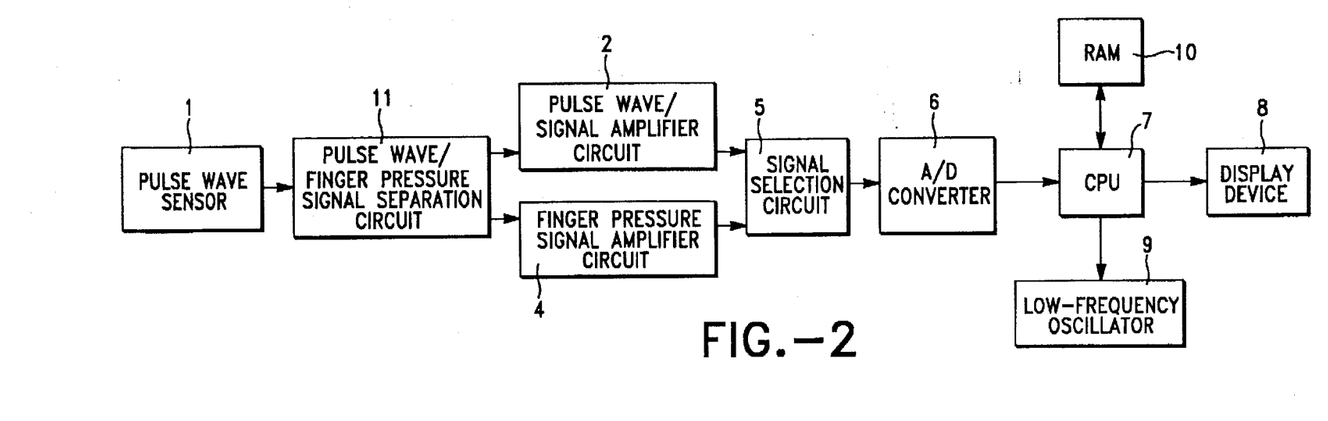
FIG. 2 is a block diagram showing the configuration of the pulse wave processing device based on the same embodiment.

FIG. 2 is a block diagram in which the pressure sensor 3 that detects the pressure is replaced with pulse wave sensor 1 that detects pulse waves, wherein the pulse wave sensor 1 detects both pulse waves and the pressure. 11 denotes a pulse wave/pressure separation circuit that separates the signals from the pulse wave sensor 1 into pulse wave signals and pressure signals. The remainder of the configuration operation is the same as the explanation of FIG. 1.

B: Electronic Wristwatch Used in this Embodiment

The following is an explanation of an embodiment in which the present invention is incorporated in an electronic wristwatch, wherein an optical means (that detects the amount of light obtained by directing light to a tissue) uses the same sensor to detect both pulse waves and pressure.

Figure 3:
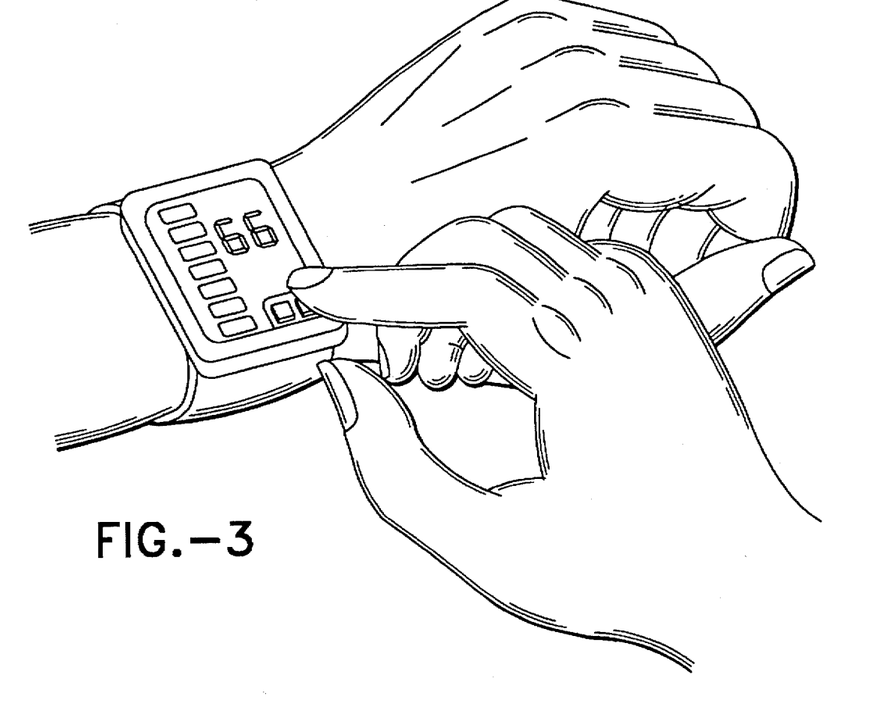
FIG. 3 shows the way in which measurements are taken when the same embodiment is used in an electronic wristwatch.

FIG. 3 shows the way in which one measures pulse waves by wearing an electronic wristwatch on the left wrist and by placing a right-hand fingertip at a prescribed position on the pulse wave sensor.

Figure 4A:
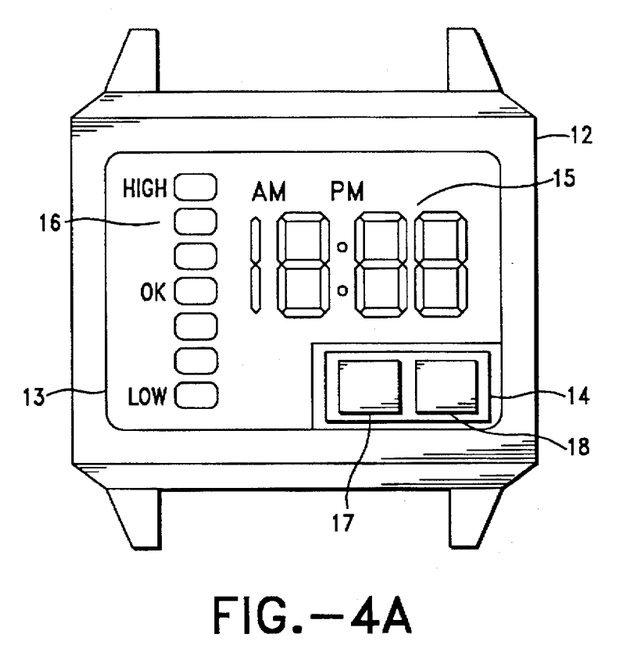
FIG. 4A is an overall configuration diagram showing the use of the same embodiment in a digital-display electronic wristwatch.

FIG. 4A is an external view of a digital-display electronic wristwatch. In the figure, 12 denotes the watch case, which is composed of a display unit 13 that displays time and pulse wave information; a pulse wave detection sensor 14, on which one places a finger; a digital display unit 15, which displays either time or pulse count information; and a signal level display unit 16, which displays pulse waveforms and pulse counts. The pulse wave detection sensor 14 includes a light-emitting device 17, composed of LEDs, and a light-receiving device 18, composed of a phototransistor.

Figure 4B:
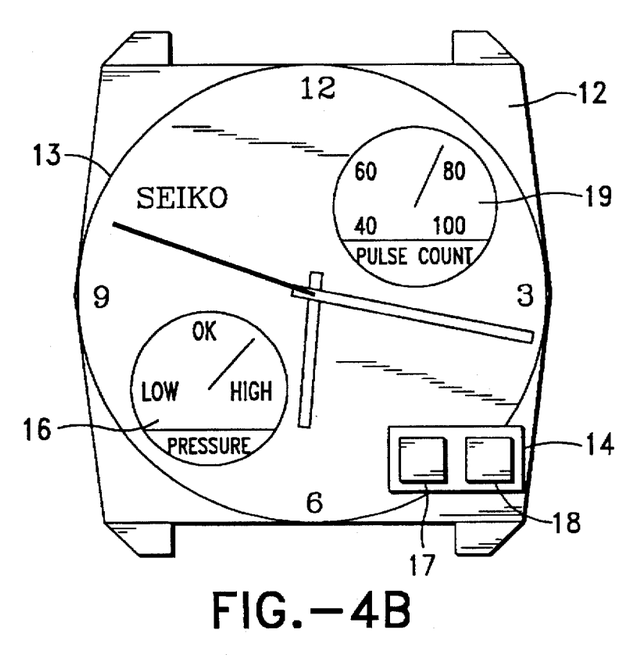
FIG. 4B is an overall configuration diagram showing the use of the same embodiment in an analog-display electronic wristwatch.

The analog watch is also shown in FIG. 4B In this figure, the signal level display unit 16, in which the pulse wave detection sensor 14 is provided, is used to indicate the pressure, the pulse wave amplitude, and pulse counts. The pulse count display unit 19 shows pulse counts.

The display processing depicted in FIGS. 4A and 4B is performed by the CPU 7.

Figure 5:
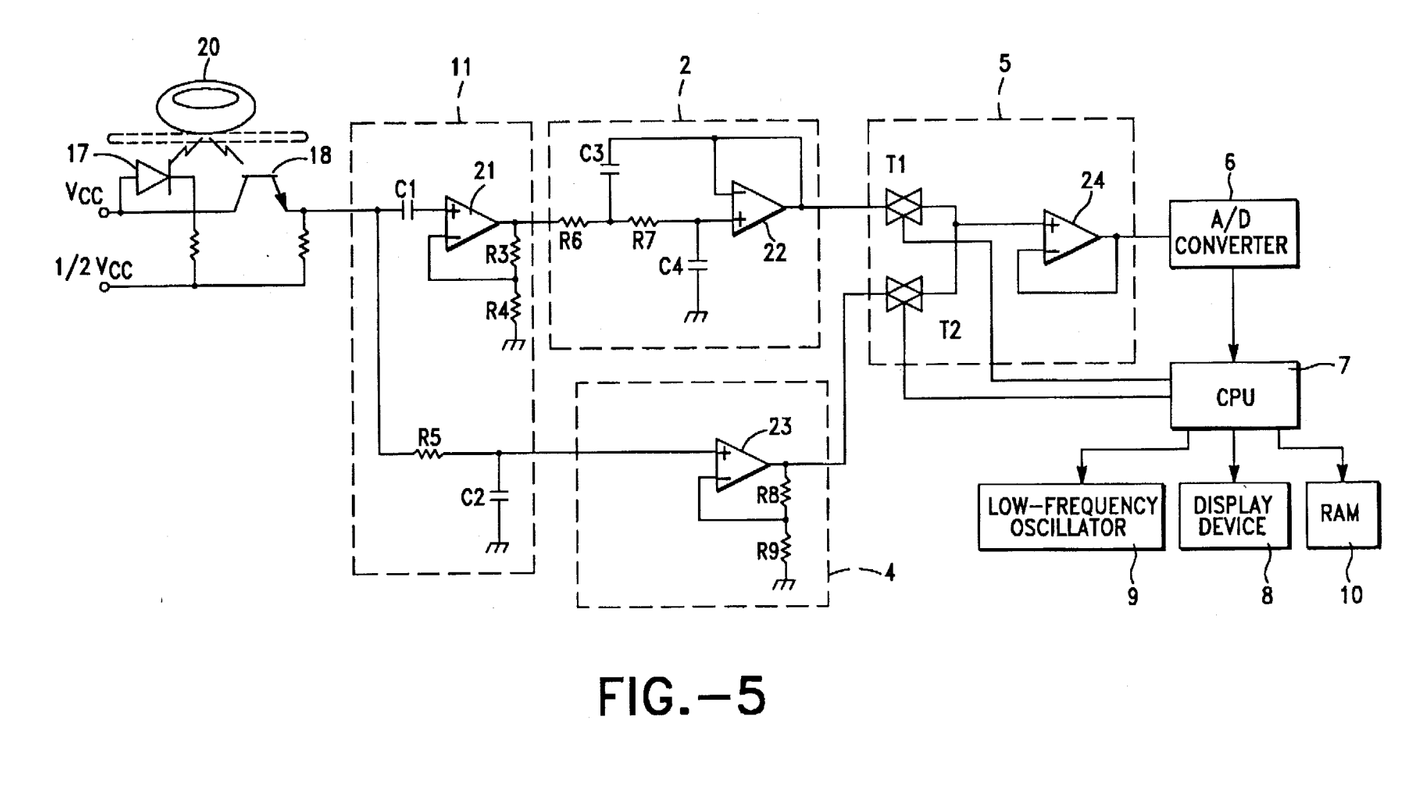
FIG. 5 is a circuit diagram showing the use of the same embodiment in an electronic wristwatch.

FIG. 5 is a circuit diagram for the electronic wristwatch that incorporates the pulse wave processing device provided inside the electronic wristwatch. The device is an embodiment of the present invention. This is a specific example of FIG. 2. The light from the LED, which is light-emitting device 17, is reflected by the hemoglobin in the blood flowing through the peripheral vessels in a finger 20. This causes a current to flow according to the amount of light captured by the light-receiving device 18. The components of this current are measured in a few V in DC, and an extremely small value of 10 mV to 100 mV in AC. The pulse wave/pressure signal separation circuit 11 uses capacitor C1 to eliminate the DC component, and uses op amp 21 to amplify the AC component only, which represents a pulse wave signal. The result is input into the low-pass filter, which is composed of op amp 22 of the pulse wave signal amplifier circuit 2, capacitors C3 and C4, and resistors R6 and R7. This removes any high-frequency ripple component that is contained in the pulse wave signal. The DC component, which represents the pressure, is extracted by using the low-pass filter composed of resistor R5 and capacitor C2, in order to remove the AC component. The result is amplified by the pressure amplifier circuit 4, composed of op amp 23 and resistors R8 and R9. Because CPU 7 performs processing by switching between pulse wave signal processing and pressure signal processing, either pulse wave signals or pressure signals are selected by the on/off action of the transfer gates T1 and T2 of the signal selection circuit 5. The selected signals are digitized by the A/D converter 6 via op amp 24 and are transmitted to the CPU 7. The CPU 7 incorporates an oscillation circuit, a division circuit that divides the oscillator output, a clock feature that keeps time and calendar, and a timing signal generator that produces various timing signals based the output of sent signals.

Figure 6:
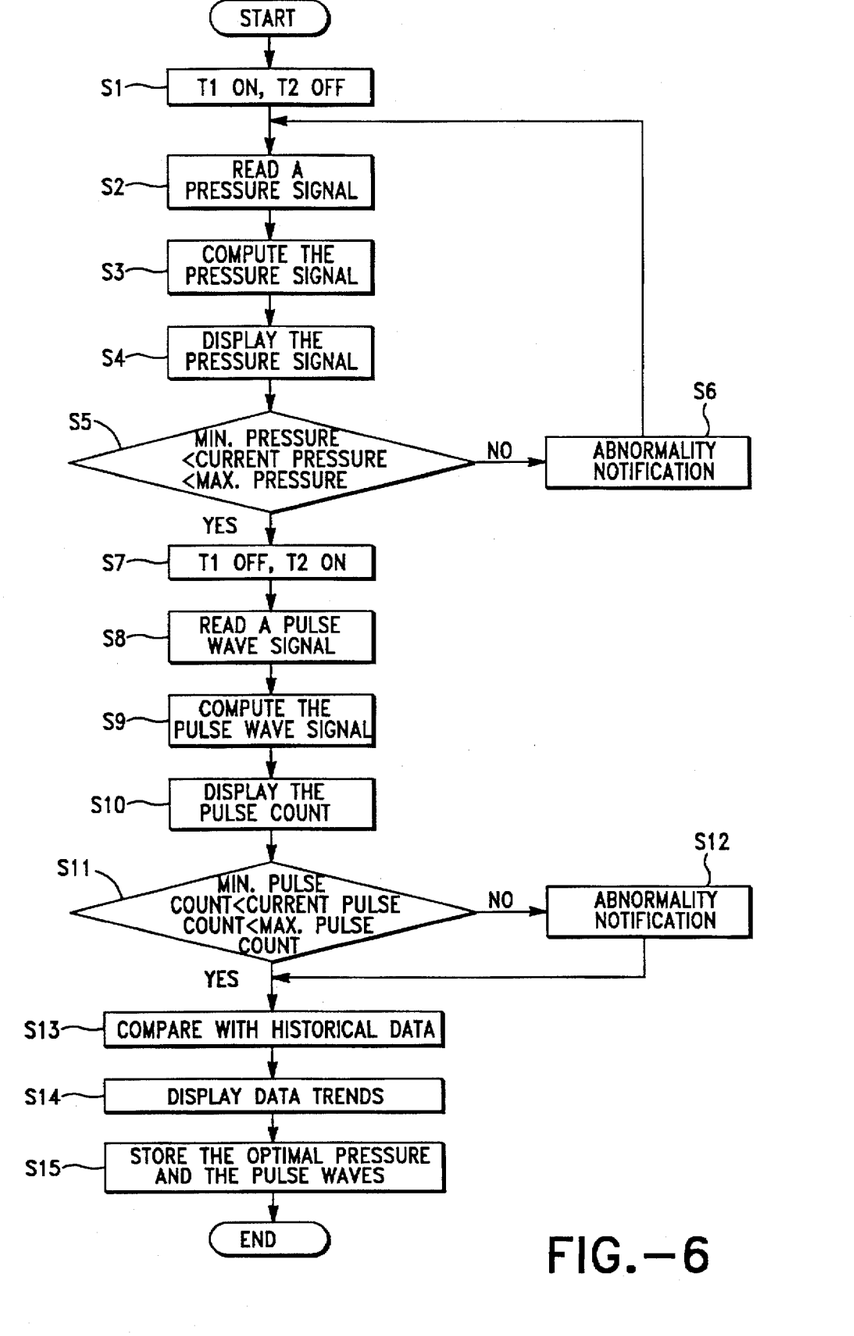
FIG. 6 is a flowchart showing the operation of CPU 9 when the same embodiments used in an electronic wristwatch.

Except for the clock feature, the CPU 7 performs its functions according to the flowchart of FIG. 6. First, when the measurement of pulse waves begins, transfer gate T1 is turned on, and transfer gate T2 is turned off, in order to read pressure information (S1); then, pressure signals are read via the A/D converter 6 (S2). Computations are performed on the pressure in order to produce a display within the 7-segment range of the signal level display unit 16 (S3). Then, the pressure level is displayed on the signal level display unit 16 of the display device (S4). A test is made to determine whether or not the current pressure is within the range defined by the minimum and maximum pressures computed in S3 (S5). If the current value is outside this range, a signal is transmitted to the low-frequency oscillator 9 (S6). This information is indicated to the operator, and pressure signals are read again (S2). Then, transfer gate T1 is turned off, and transfer gate T2 is turned on (S7). Pulse wave signals are read via the A/D converter 6 (S8). From the pulse wave signals, a conversion is performed in order to determine the pulse count per minute (e.g., a 60-second/pulse wave cycle) (S9). The results are displayed on either the digital display unit 15 or pulse count display unit 19 (S10). The current pulse count is compared with minimum and maximum pulse counts, which are previously stored in RAM (S11). If the current pulse count is outside this range, a signal is transmitted to the low-frequency oscillator 9 (S12), and a sound is generated to notify the operator. Then, past pulse waves and pressure data, stored in RAM 10, are compared by computation with current values (S13). For the comparison computation, the operator can set options for replacing historical pulse wave and pressure data, which are subject to computation, with current data, or for using the averages of several previous readings. As a result of the comparison computation processing, the next items are displayed on the signal level display unit 16 (S14). Displays (a)–(c) can be selected in terms of display modes (a)–(c) by manipulating the operating switches on the electronic wristwatch. Based on this manipulation, the CPU 7 performs the required display switching operations.

(a): Indicate the "high" direction if there is a rising tendency in optimal pressure; if there is a declining tendency, show "low."

(b): Indicate the "high" direction if there is a rising tendency in pressure amplitude; if there is a declining tendency, show "low."

(c) Calculate a pulse count from pulse waves. Indicate the "high" direction if there is a rising tendency in pulse count; if there is a declining tendency, show "low."

The current pulse wave and pressure are stored in RAM 10 (S15). Upon completion of these operations, the same sequence of operations is repeated.

Figure 7:
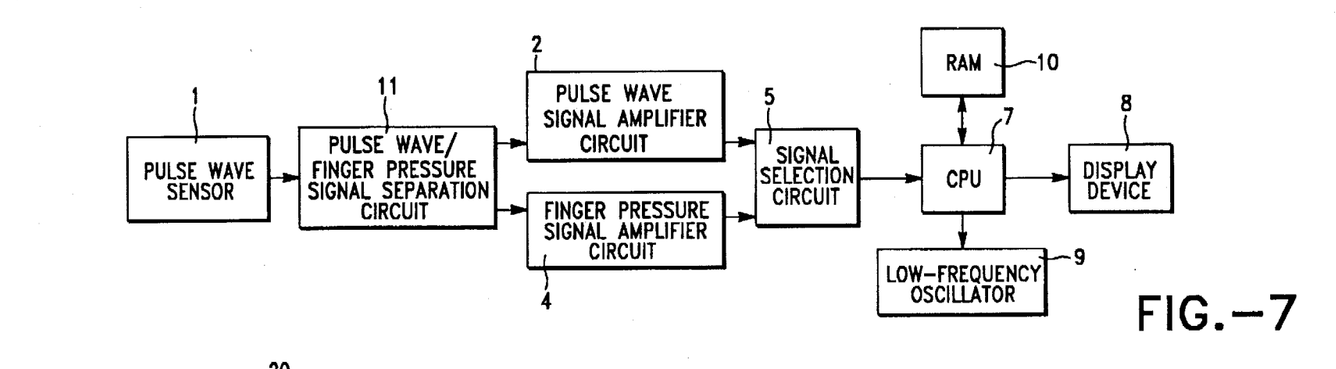
FIG. 7 is a block diagram showing the configuration of the electronic wristwatch when the same embodiment is used in an electronic wristwatch.
Figure 8:
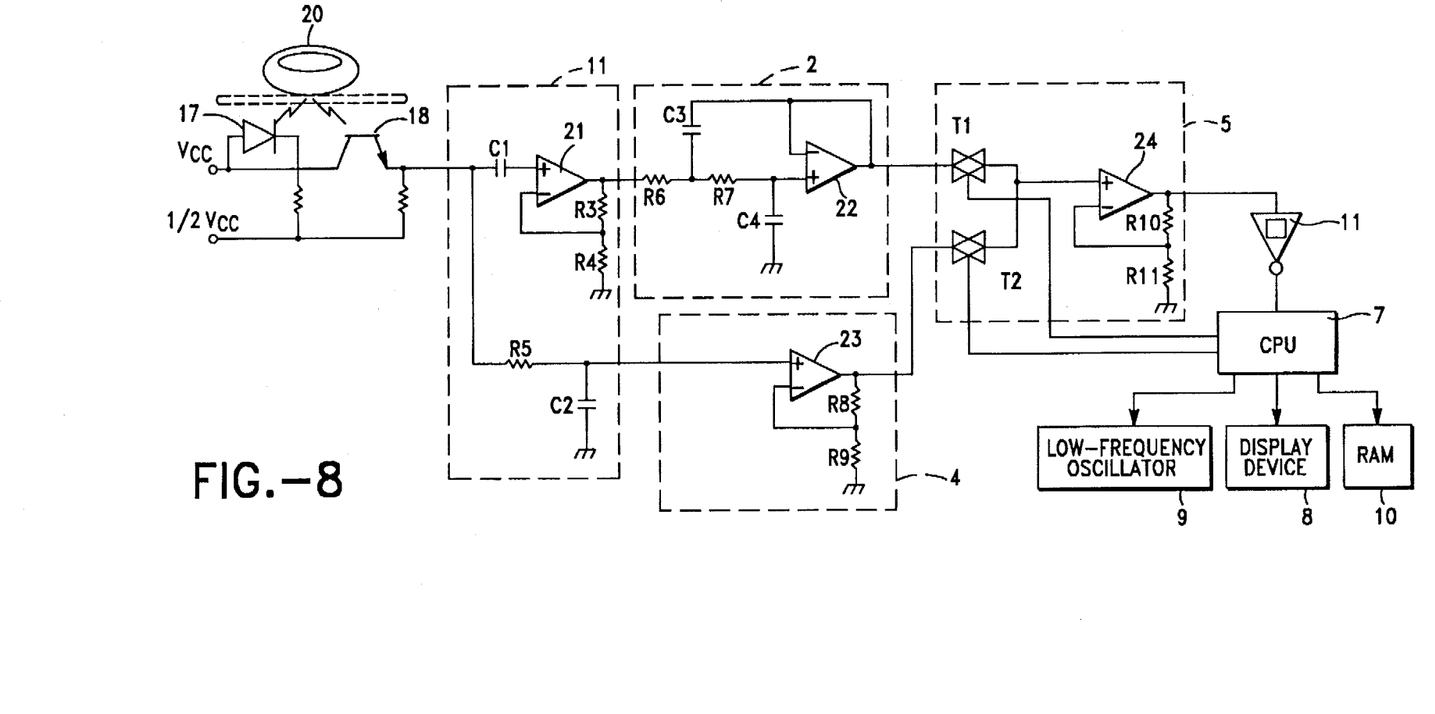
FIG. 8 is a circuit diagram showing the configuration of the electronic wristwatch when the same embodiment is used in an electronic wristwatch.

FIG. 7 is a block diagram showing a pulse wave processing device, incorporated in the above electronic wristwatch, used in an embodiment of the present invention, in which an A/D converter 6 is not used. FIG. 8 is a circuit diagram for this device. Here, a binarization circuit 11 is used in place of A/D converter 6. The op amp 24 of the signal selection circuit 5 amplifies the pulse wave signals up to the level of the power supply voltage supplied to the pulse wave processing device. The amplified pulse wave signals are converted in the binarization circuit 11, for which a threshold voltage is set, on the basis of whether or not a given signal is higher or lower than the threshold voltage. The amplified pulse wave signals are converted into binary rectangular waves including a ground level and a power supply voltage level. The results are transmitted to the CPU 7. The threshold voltage is set closer to the power supply voltage than to the voltage which is midpoint between the ground level and the power supply voltage level. For this reason, the binary value of this rectangular wave indicates pulses when pulse wave signals are processed. When pressure signals are processed, the binary value indicates whether or not measurements can be performed. In other words, if the amplitude of a pulse wave signal is less than the threshold voltage, the CPU determines that the signal is not measurable. The remainder of the configurations in FIGS. 7 and 8 are identical to those in FIGS. 2 and 5.

Figure 9A:
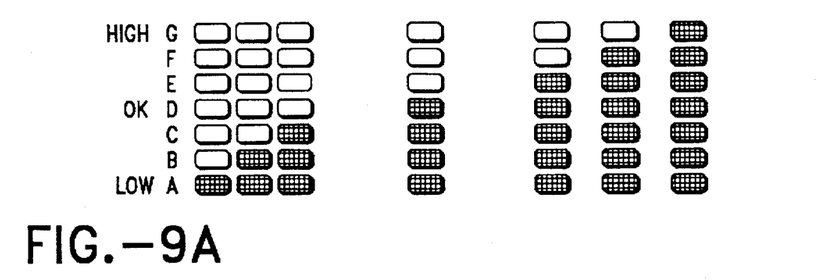
FIG. 9A is a display diagram that corresponds to FIG. 9B.
Figure 9B:
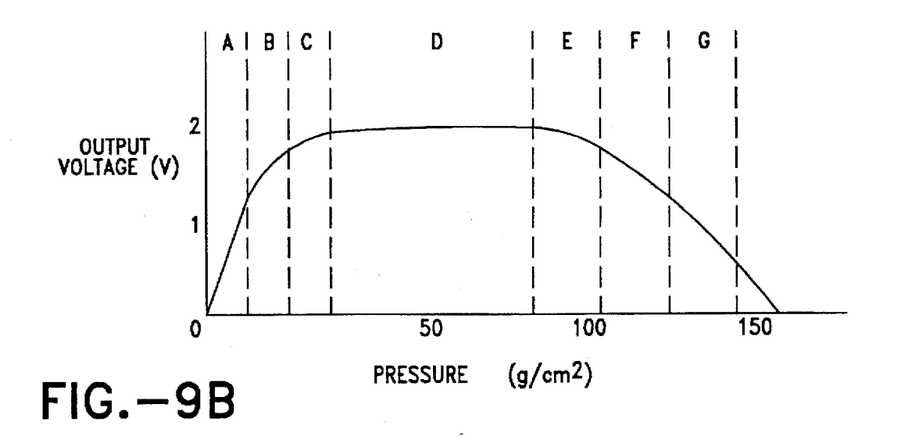
FIG. 9B shows the relationship between the pressure and the voltage when the same embodiment is used in an electronic wristwatch.
Figure 9C:
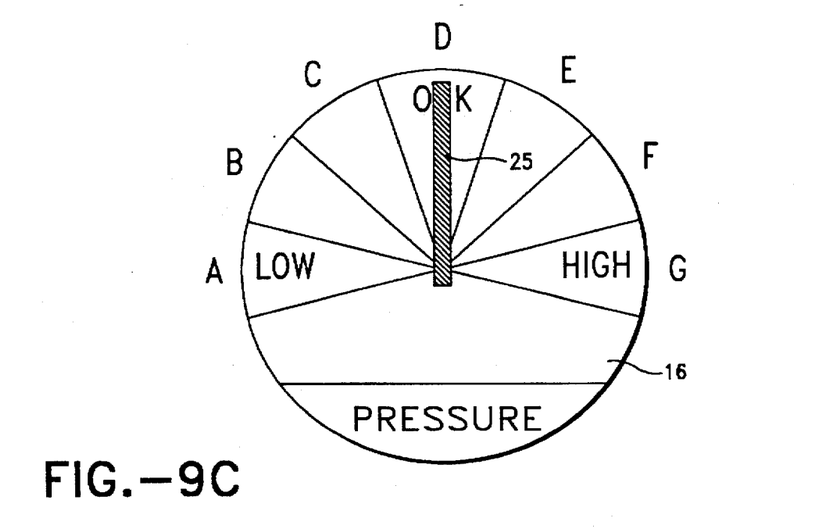
FIG. 9C is an analog display diagram that corresponds to FIG. 9B.

FIG. 9B is a graph plotting the output from the pressure signal amplifier circuit 4, relative to the pressure, on the horizontal axis, and the output from the pulse wave signal amplifier circuit 2 on the vertical axis. The intervals in which items A–G for signal level display unit 16 are displayed are determined according to the pressure. The intervals A–G in FIG. 9B correspond to items A–G for digital signal level display unit 16 in FIG. 9A. FIG. 9C is applicable to analog display. As in the case of digital display, in FIG. 9C also, the direction indicated by the pressure indicator 25 varies according to the intervals A–G. The CPU 7 determines which display area is to be used.

C: Variations (1) The embodiment section described the computation processing method that is designed to calculate a pulse count from the original form of pulse waves. However, other types of calculations can also be performed under the present invention.

(2) In the embodiment, the pulse wave detection sensor 14 was incorporated into the watch case 12. However, these units can be separated and can be placed at any detection site at which light can be shone on blood vessels. For example, the root of a finger, the radial artery, or the ear can be used.

(3) The embodiment included a photoelectric sensor for pulse wave detection sensor 14. However, any of the following sensors can also be used: piezoelectric, ultrasonic, or impedance.

(4) RAM 10 can be made of either writable EEPROM or flash memory.

(5) Whereas the embodiment showed a signal level display unit 16 that notifies the operator by producing either a digital or analog display, notifications can be generated in terms of color changes in a light source, such as an LED. Likewise, instead of a visual display, either voice or change in sound frequency can be employed.

Figure 10:
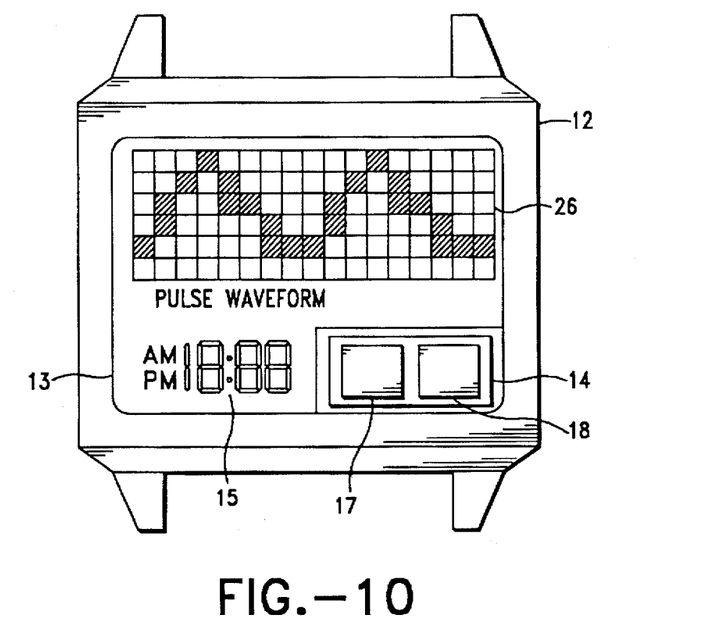
FIG. 10 is an external view configuration diagram showing the use of the embodiment in an electronic wristwatch; it shows pulse waveforms.
Figure 11:
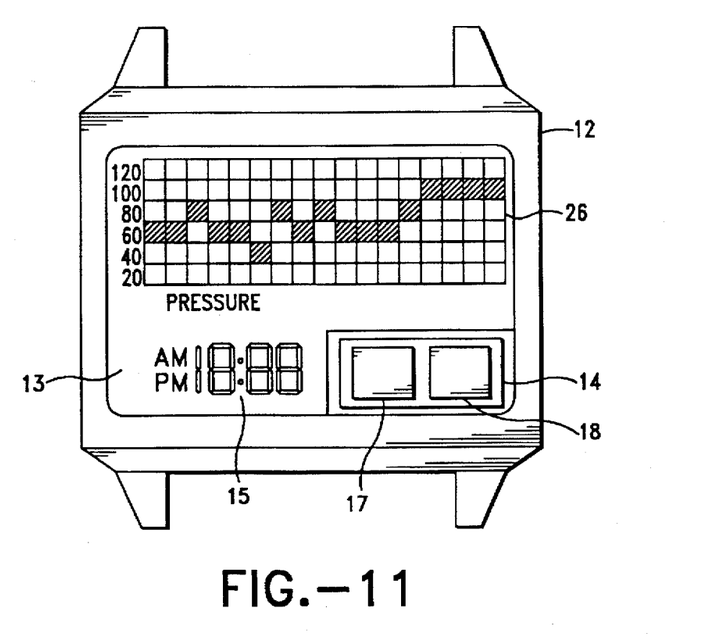
FIG. 11 is an external view configuration diagram showing the use of the embodiment in an electronic wristwatch; it shows changes in the pressure.
Figure 12:
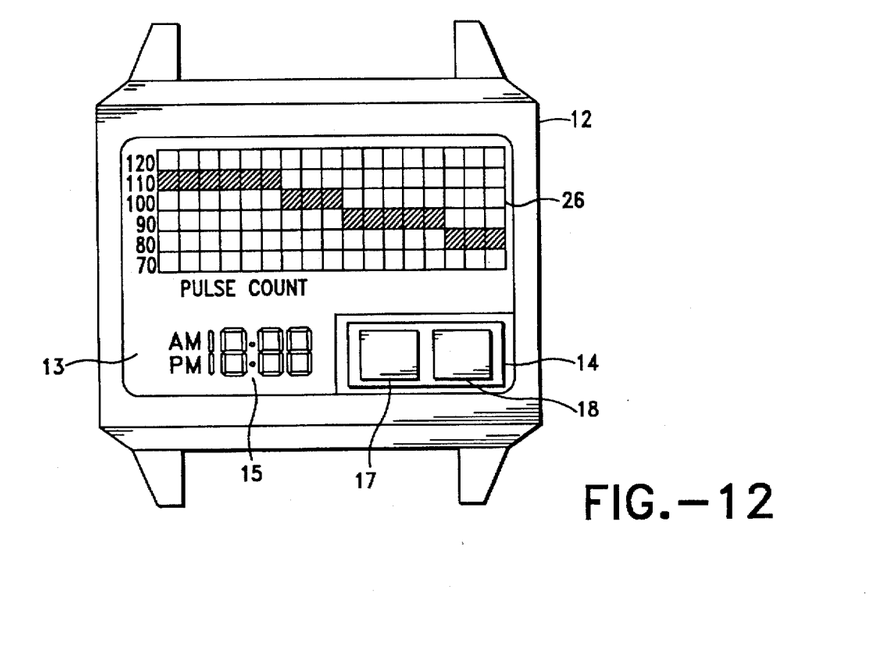
FIG. 12 is external view configuration diagram showing the use of the embodiment in an electronic wristwatch; it shows changes in pulses.

(6) FIG. 10 shows a digital display method of indicating time-dependent change in detected pulse waves and pressure, or in analyzed pulse count. FIG. 10 shows the case where a pulse waveform itself is displayed on a pulse wave/pressure change display unit 26 using a matrix LED. FIG. 11 shows the case where the previous 16 pressure readings and the current pressure are displayed on a pulse wave/pressure change display unit 26 using a matrix LCD, by storing the pressure on each measurement. The pressure is plotted on the y-axis, and time is plotted on the x-axis. Time increases from left to right, so that the rightmost time value is the current pressure. FIG. 12 shows the case where the previous 16 pulse counts and the current pulse count are displayed on a pulse wave/pressure change display unit 26 using a matrix LCD, by storing an analyzed pulse count on each measurement. Pulse counts are plotted on the y-axis, and time is plotted on the x-axis. Time increases from left to right, so that the rightmost time value is the current pulse count. From these data, the operator can confirm change in pulse waveforms, change in pressure, and change in pulse count, and determine any emerging patterns. The CPU 7 regulates the time-series display of pulse waves, pressure, and pulse counts that is produced on the matrix LCD.

(7) The signal level display unit 16 can be separated into individual display units, to be placed at other locations.

(8) The present invention is characterized in that it is capable of detecting the pressure so as to obtain accurate pulse waves. Therefore, it can be used in configurations such as the blood pressure meter that calculates the blood pressure from pulse wave propagation time, a blood oxygen concentration meter, or acceleration pulse wave meter.

POSSIBILITY OF INDUSTRIAL APPLICATIONS

As described above, the pulse wave processing device of this invention can be used in small electronic devices, such as an electronic wristwatch. It can also be used in configurations such as a blood pressure meter that calculates the blood pressure from pulse wave propagation time, a blood oxygen concentration meter, or an acceleration pulse wave meter.

This invention makes it possible to determine the condition of a human body and to perform health management. Therefore, the present invention can be used in medical instruments and related equipment.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pulse wave processing device, comprising:

pulse wave detection means for detecting a pulse wave from a part of a living body that applies a pressure at said pulse wave detection means;

pressure detection means for detecting the pressure applied at said pulse wave detection means by the living body;

pulse wave processing means for processing an output of said pulse wave detection means and an output of said pressure detection means to generate an output signal selectively representative of said detected pressure and said detected pulse wave, said pulse wave processing means comprising:

testing means for testing whether the pressure detected by said pressure detection means is within a first predetermined range for determining detectability of the pulse wave of the living body, computing means for computing a pulse count of the living body, based on the pulse wave detected by said pulse wave detection means, if the pressure detected by said pressure detection means is within the first predetermined range, memory means for storing past pulse wave data and past pressure data, comparison means for comparing current pulse wave data from said pulse wave detection means and current pressure data from said pressure detection means, respectively, with the past pulse wave data and the past pressure data stored in said memory means, so that an optimal pressure and an optimal pulse wave are determined, and analyzing means for analyzing the current and past pulse wave data and pressure data for determining the health status of the living body;

display means for displaying the output signal of said pulse wave processing means, said displayed output signal selectively representing said detected pressure and said detected pulse wave; and notification means for providing a first notification if the pressure detected by said pressure detection means is outside the first predetermined range and for providing a second notification if the pulse count computed by said computing means is outside a second predetermined range.

2. The pulse wave processing device of claim 1, wherein said display means includes means for notifying an operator of pulse wave detectability based on an output of said testing means.

3. The pulse wave processing device of claim 2, wherein the display means includes means for indicating the pressure detected by the detection means in analog fore.

4. The pulse wave processing device of claim 2, wherein said display means includes means for indicating the pressure detected by said pressure detection means in digital form.

5. The pulse wave processing device of claim 2, wherein the display means includes means for indicating the pressure detected by the detection means in the form of color changes.

6. The pulse wave processing device of claim 2, wherein the display means includes means for indicating the pressure detected by the detection means in the form of sound changes.

7. The pulse wave processing device of claim 2, wherein the display means includes means for indicating the pressure detected by the detection means in the form of voice.

8. The pulse wave processing device of claim 2, wherein said pulse wave detection means detects the pulse waves by detecting the amount of reflected light when light is directed onto the part of the living body.

9. The pulse wave processing device of claim 2, wherein the pulse wave detection means detects the pulse waves by detecting the amount of transmitted light when light is directed onto the part of the human body.

* * * * *